US00PP20070P2

(12) United States Plant Patent
Hartman

(10) Patent No.: US PP20,070 P2
(45) Date of Patent: Jun. 9, 2009

(54) ***CALADIUM* PLANT NAMED 'ROSE GLOW'**

(50) Latin Name: *Caladium×hortulanum*
Varietal Denomination: Rose Glow

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 12/070,569

(22) Filed: Feb. 19, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—June Hwu
(74) *Attorney, Agent, or Firm*—C. A. Whealy

(57) ABSTRACT

A new and distinct cultivar of *Caladium* plant named 'Rose Glow', characterized by its tall and upright plant habit; vigorous and dense growth habit; fancy-type leaves that are red purple in color in the center with green-colored borders and dark green-colored margins.

3 Drawing Sheets

Botanical designation: *Caladium×hortulanum.*
Cultivar denomination: 'ROSE GLOW'.

BACKGROUND OF THE INVENTION

The present invention relates to a new and distinct cultivar of *Caladium* plant, botanically known as *Caladium× hortulanum,* commercially referred to as a fancy leaf-type *Caladium* and hereinafter referred to by the name 'Rose Glow'.

The objective of the Inventor's breeding program is to create new *Caladium* cultivars that have uniform plant habit, exceptional performance and attractive foliage coloration.

The new *Caladium* originated from a cross-pollination made by the Inventor in June, 2001, in Lake Placid, Fla. of the *Caladium×hortulanum* cultivar Aaron, not patented, as the female, or seed, parent with the *Caladium×hortulanum* cultivar Freida Hemple, not patented, as the male, or pollen, parent. The new *Caladium* was discovered and selected by the Inventor as a single plant within the progeny of the stated cross-pollination in a controlled environment in Lake Placid, Fla. on Jun. 15, 2002.

Asexual reproduction of the new cultivar by tuber divisions in a controlled environment in Lake Placid, Fla. since Apr. 5, 2003 has shown that the unique features of this new *Caladium* are stable and reproduced true to type in successive generations of asexual reproduction.

SUMMARY OF THE INVENTION

The cultivar Rose Glow has not been observed under all possible environmental conditions. The phenotype may vary somewhat with variations in environment such as temperature and light intensity, without, however, any variance in genotype.

The following traits have been repeatedly observed and are determined to be the unique characteristics of 'Rose Glow'. These characteristics in combination distinguish 'Rose Glow' as a new and distinct cultivar of *Caladium*:

1. Tall and upright plant habit.
2. Vigorous and dense growth habit.

3. Fancy-type leaves that are red purple in color in the center with green-colored borders and dark green-colored margins.

Plants of the new *Caladium* differ from plants of the female parent, the cultivar Aaron, primarily in foliage coloration as plants of the cultivar Aaron have white-colored leaves with dark green-colored marginal areas.

Plants of the new *Caladium* differ from plants of the male parent, the cultivar Freida Hemple, primarily in foliage coloration as plants of the cultivar Freida Hemple have bright red-colored leaves with dark green-colored margins.

Plants of the new *Caladium* can also be compared to plants of the cultivar Rosebud, not patented. In side-by-side comparisons conducted in Lake Placid, Fla., plants of the new *Caladium* differed from plants of the cultivar Rosebud in the following characteristics:

1. Plants of the new *Caladium* were taller and more vigorous than plants of the cultivar Rosebud.
2. Plants of the new *Caladium* and the cultivar Rosebud differed in leaf coloration as plants of the cultivar Rosebud had leaves that are pink in color in the center with light green-colored borders and dark green-colored margins.

BRIEF DESCRIPTION OF THE PHOTOGRAPHS

The accompanying photographs illustrate the overall appearance of the new *Caladium*. These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet is a side perspective view of a typical plant of 'Rose Glow' grown in a container in a shadehouse.

The photograph at the top of the second sheet is a side perspective view of typical plants of 'Freida Hemple' (left), 'Rose Glow' (center) and 'Aaron' (right) grown in a shadehouse.

The photograph at the bottom of the third sheet is a side perspective view of typical plants of 'Rosebud' (left) and 'Rose Glow' (right) grown in a shadehouse.

The photograph at the top of the fourth sheet is a top perspective view of typical plants of 'Rose Glow' grown in an outdoor nursery.

The photograph at the bottom of the fourth sheet is a close-up view of typical leaf petioles, tubers and roots of 'Rose Glow'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in 15-cm containers in Avon Park, Fla. during the spring in a polypropylene-covered shadehouse and plants grown in ground beds in Zolfo Springs, Fla. during the late summer in an outdoor nursery. All plants were grown under conditions and practices which approximate those generally used in commercial *Caladium* production. During the production of the plants, day temperatures ranged from about 20° C. to 30° C., night temperatures ranged from about 10° C., to 20° C. and light levels were about 8,000 foot-candles (shadehouse) or 10,000 to 12,000 foot-candles (outdoor nursery). Plants grown in the shadehouse were about seven weeks from planting tubers when the photographs and the detailed description were taken. Plants grown in the outdoor nursery were about four months from planting tuber pieces when the photographs and the detailed description were taken.

Botanical classification: *Caladium×hortulanum* cultivar Rose Glow.

Parentage:

*Female, or seed, parent.*—*Caladium×hortulanum* cultivar Aaron, not patented.

*Male, or pollen, parent.*—*Caladium×hortulanum* cultivar Freida Hemple, not patented.

Propagation:

*Type.*—By tubers and by tuber divisions.

*Time to initiate roots, summer.*—About seven to ten days at 32° C.

*Time to initiate roots, winter.*—About two to three weeks at 24° C.

*Tuber description.*—Number of buds per tuber, shadehouse-grown plants: About 14 actively growing buds/shoots. Number of buds per tuber, outdoor nursery-grown plants: About two to three actively growing buds/shoots. Height: About 3.8 cm. Diameter: About 5.8 cm. Texture: Thick, starchy; somewhat brittle. Color: Epidermis, between N199D to 199A; interior, 4C to 4D. Root description: Dense, thick and white fleshy roots.

Plant description:

*Plant type.*—Herbaceous perennial.

*Plant/growth habit.*—Tall and upright plant habit; inverted triangle. Vigorous, dense growth habit; suitable for 15-cm to 25-cm containers. Leaf petioles arising from tubers; petioles mostly upright and outwardly arching with development.

*Plant height, from soil level to top of leaf plane, shadehouse-grown plants.*—About 32 cm.

*Plant height, from soil level to top of inflorescences, shadehouse-grown plants.*—About 31 cm.

*Plant diameter or spread, shadehouse-grown plants.*—About 48 cm.

*Plant height, from soil level to top of leaf plane, outdoor nursery-grown plants.*—About 61 cm to 70 cm.

*Plant height, from soil level to top of inflorescences, outdoor nursery-grown plants.*—Inflorescences not observed on plants grown in the outdoor nursery.

*Plant diameter or spread, outdoor nursery-grown plants.*—About 65 cm to 72 cm.

*Cataphylls* (*only observed on shadehouse-grown plants*).—Length: About 6 cm to 9.5 cm. Width: About 1.8 cm. Shape: Linear. Apex: Acute. Base: Sheathing the stem. Color, inner and outer surfaces: N170D variably streaked with N186A; with development, color becoming closer to 199A to 199B tinted with 183B.

Foliage description:

*Length, shadehouse-grown plants*—About 17 cm to 29 cm.

*Width, shadehouse-grown plants* (*fattened*).—About 13.5 cm to 20 cm.

*Length, outdoor nursery-grown plant.*—About 24 cm to 35 cm.

*Width, outdoor nursery-grown plants* (*flattened*).—About 13 cm to 16.5 cm.

*Shape.*—Ovate.

*Apex.*—Acuminate.

*Base.*—Sagittate to peltate.

*Margin.*—Entire; mostly flat with some broad undulations.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Ground: 147A to 147B with 146B cast. Margins: 147A. Center: 53B to 53C; basal notch, 53B. Venation: Midrib and primary veins, between 155D and 56A speckled and streaked with 53B to 53C. Developing leaves, lower surface: Ground: 147B tinted with 191A. Center: 59C. Venation: Midrib, 155C tinged with 145D; primary veins, 155C tinged with 156D and faintly tinged with 55D. Fully developed leaves, upper surface: Ground: 147C tinted with 191A to 191B. Margins: Darker and more green than 147A. Center: 53B to 53C tinged with 184C to 184D. Venation: Midrib, between 196D and 155C speckled and streaked with 53C to 53D and 184C; primary veins, between 194D and 155C speckled and streaked with 147A or between 184C and 53D. Fully developed leaves, lower surface: Ground: Between 191A and 147B. Center: 59C flecked with 145C to 145D. Venation: Midrib, 155A tinged with 145D; primary veins, 155C tinged with 145D.

*Color, outdoor nursery-grown plants.*—Developing leaves, upper surface: Ground: 147A to 147B speckled with 145D. Margins: 147A to 147B. Center: 53A to 53B; basal notch, 59A. Venation: Midrib, 155D speckled with 53B; primary veins, 150D speckled and streaked with 53B. Developing leaves, lower surface: Ground: 147B with 138B cast. Center: 60A to 60B flecked with 145D; basal notch, 59A. Venation: Midrib, 155C tinged with 145D; primary veins, between 145C to 145D and 155C. Fully developed leaves, upper surface: Ground: 147A flecked with 155A or 145D. Margins: 147A. Center: 53B to 53C; basal notch, 59A. Venation: Midrib, 155D speckled and streaked with 53A to 53B; primary veins, between 155D and 150D speckled and streaked with 53B. Fully developed leaves, lower surface: Ground: 147B with 138B cast. Center: Between 60A and 59C flecked with 145D; basal notch, 59A. Venation: Midrib, 155C tinged with 145C; primary veins, 145C to 145D often tinged with 49C.

*Petiole.*—Aspect: Mostly erect, outwardly arching with development. Length, shadehouse-grown plants: About 27 to 34 cm. Diameter, distal, shadehouse-grown plants: About 4 mm. Diameter, proximal, shadehouse-grown plants: About 8 mm. Length, outdoor nursery-grown plants: About 34 cm to 58 cm. Diameter, distal, outdoor nursery-grown plants: About 6 mm. Diameter, proximal, outdoor nursery-grown plants: About 1.4 cm. Strength: Strong; flexible. Color, distal, shadehouse-grown plants: Between 147C and 146C. Color, proximal, shadehouse-grown plants: Between 146B and 147B to N170D and variably streaked with N186A. Color, distal, outdoor nursery-grown plants: 147B and variably streaked with N186A. Color, proximal, outdoor nursery-grown plants: Between N170D and 27D, variably streaked with 147B and barred with N186A. Wing length, shadehouse-grown plants: About 4.5 cm to 6 cm. Wing diameter, shadehouse-grown plants: About 1 cm. Wing length, outdoor nursery-grown plants: About 12.8 cm. Wing diameter, outdoor nursery-grown plants: About 1 cm. Wing color, shadehouse-grown plants: 147B tinged with N170D and variably streaked with N186A. Wing color, outdoor nursery-grown plants: Between N170D and 27D, variably streaked with 147B and barred with N186A.

Inflorescence description: Inflorescences only observed on shadehouse-grown plants.

*Inflorescence arrangement.*—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about seven weeks after growth commences. Inflorescences last about three days before fading; inflorescences persistent.

*Spathe.*—Length: About 13 cm. Width, distal: About 4.5 cm. Width, proximal: About 2.5 cm. Shape: Ovate. Apex: Acute. Base: Tapering. Margin: Entire. Texture, upper and lower surfaces: Smooth, glabrous. Color: Front surface: Upper two-thirds: Between 145D and 155C. Color becoming closer to between 199D and N199B with development. Lower one-third: 138B to 138C streaked with 138B. Color becoming closer to 147B streaked with 194B to 194C with development. Rear surface: Upper two-thirds: 145D to 145B. Lower one-third: 147B to 147D streaked with 194B to 194C. Spadix: Length, entire spadix: About 6.5 cm. Length, male flower zone: About 3.9 cm. Length, sterile flower zone: About 9 mm. Length, female flower zone: About 1.4 cm. Diameter, male flower zone: About 8 mm. Diameter, sterile flower zone: About 7 mm. Diameter, female flower zone: About 8 mm. Shape: Spindle-shaped to columnar. Apex: Obtuse. Base: Obtuse. Aspect: Upright. Color, mature, male zone: 158A. Color, mature, sterile zone: 158A Color, mature, female zone: 11C. Male flowers: Quantity per spadix: About 122. Shape: Obovate. Height: About 3 mm. Diameter: About 2.5 mm. Anther color: Close to 157D. Amount of pollen: None observed. Female flowers: Quantity per spadix: About 100. Shape: Obovate. Height: About 2.5 mm. Diameter: About 2 mm. Stigma color: 11C. Ovary color: 155C. Scape: Length: About 19 cm. Diameter: About 6 mm. Strength: Sturdy; flexible. Aspect: Erect or slightly curved. Texture: Smooth, glabrous; glaucous. Color: 147B streaked with N186A.

*Seed and fruit.*—Seed and fruit development has not been observed on plants of the new *Caladium*.

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium*.

Temperature tolerance: Plants of the new *Caladium* have been observed to be tolerant to temperatures ranging from about 7° C. to about 40° C.

It is claimed:

1. A new and distinct *Caladium* plant named 'Rose Glow' as illustrated and described.

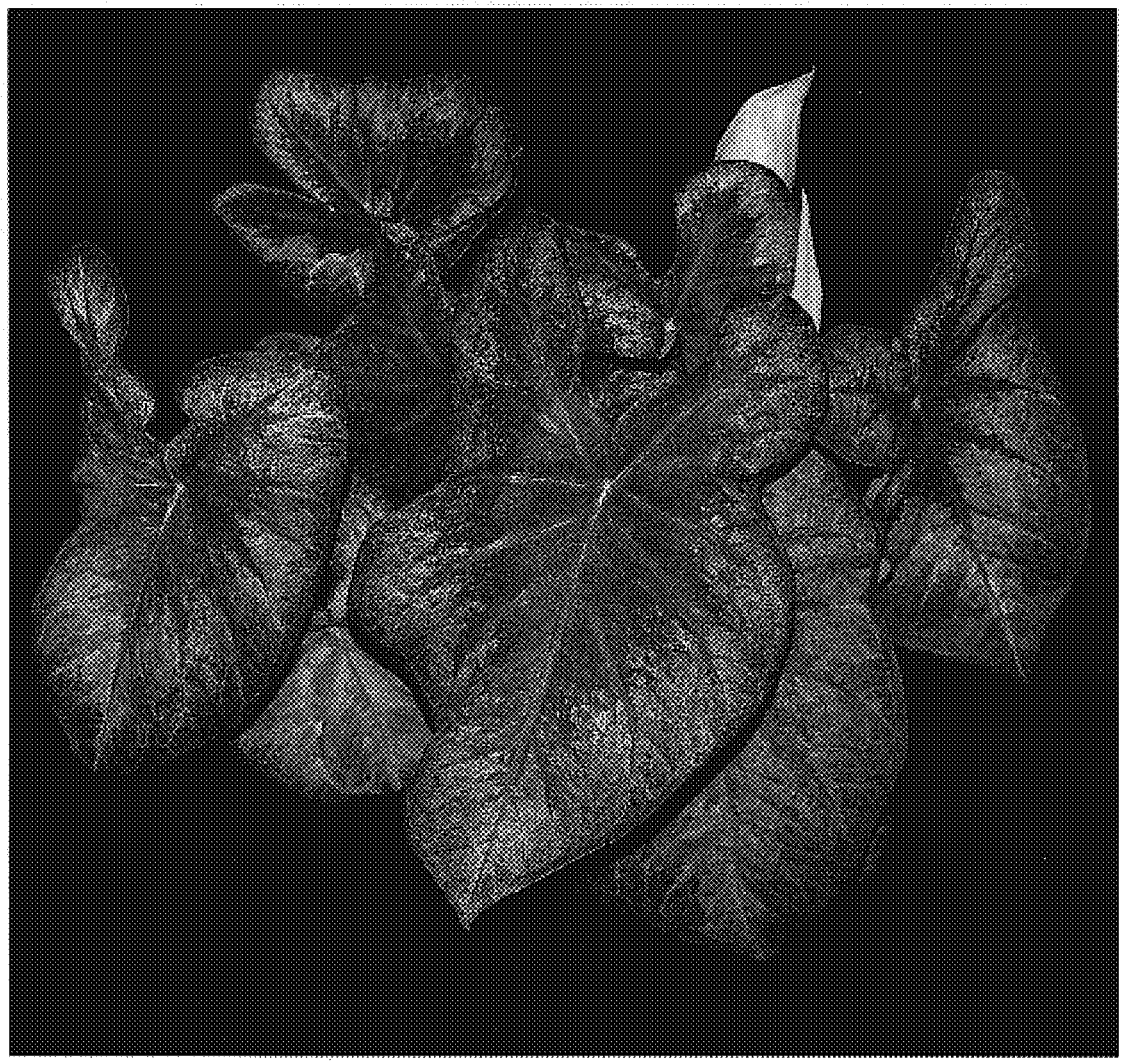

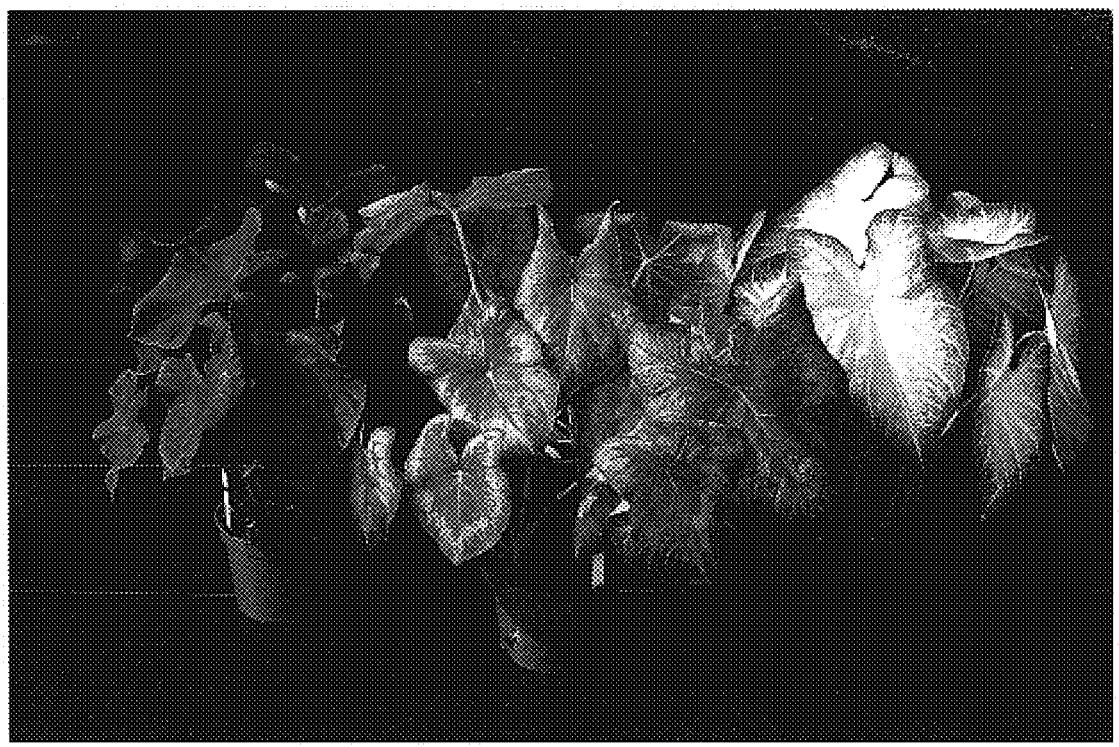
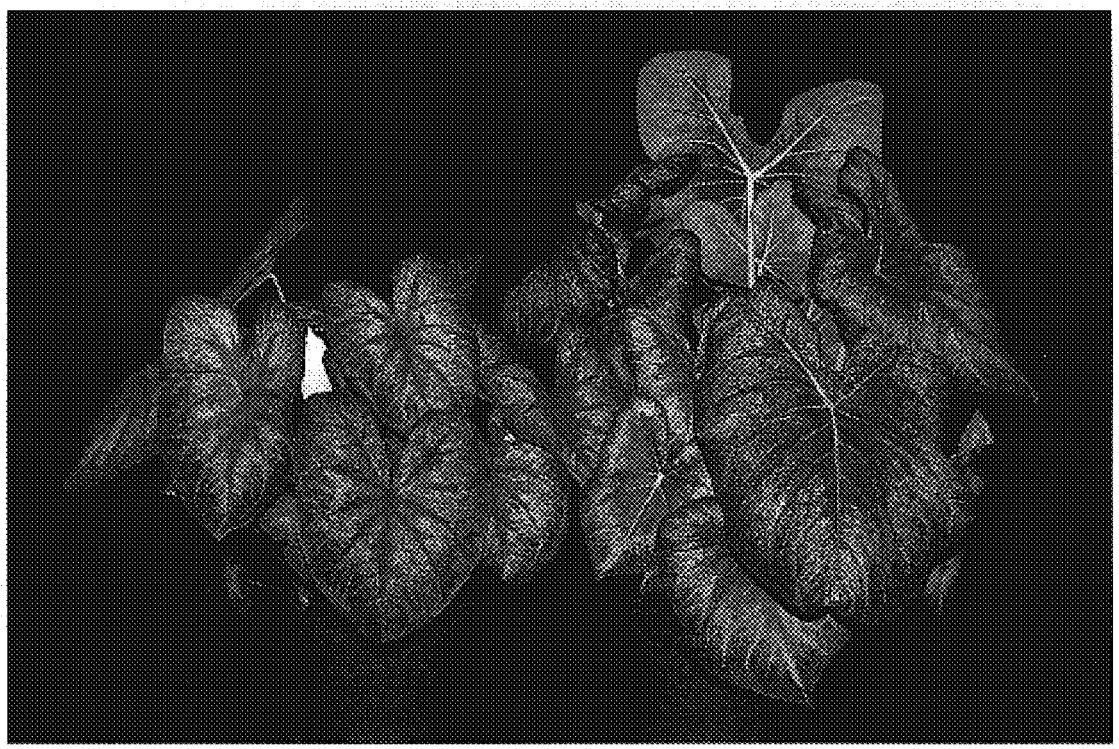

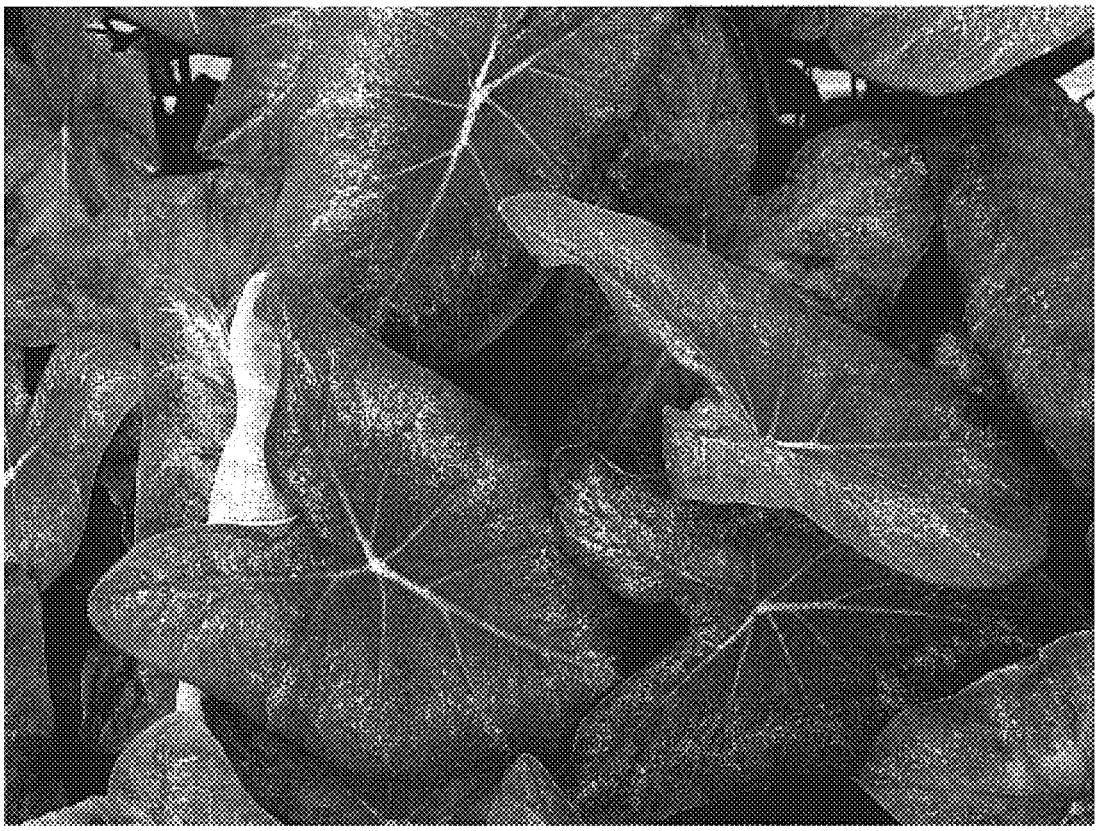
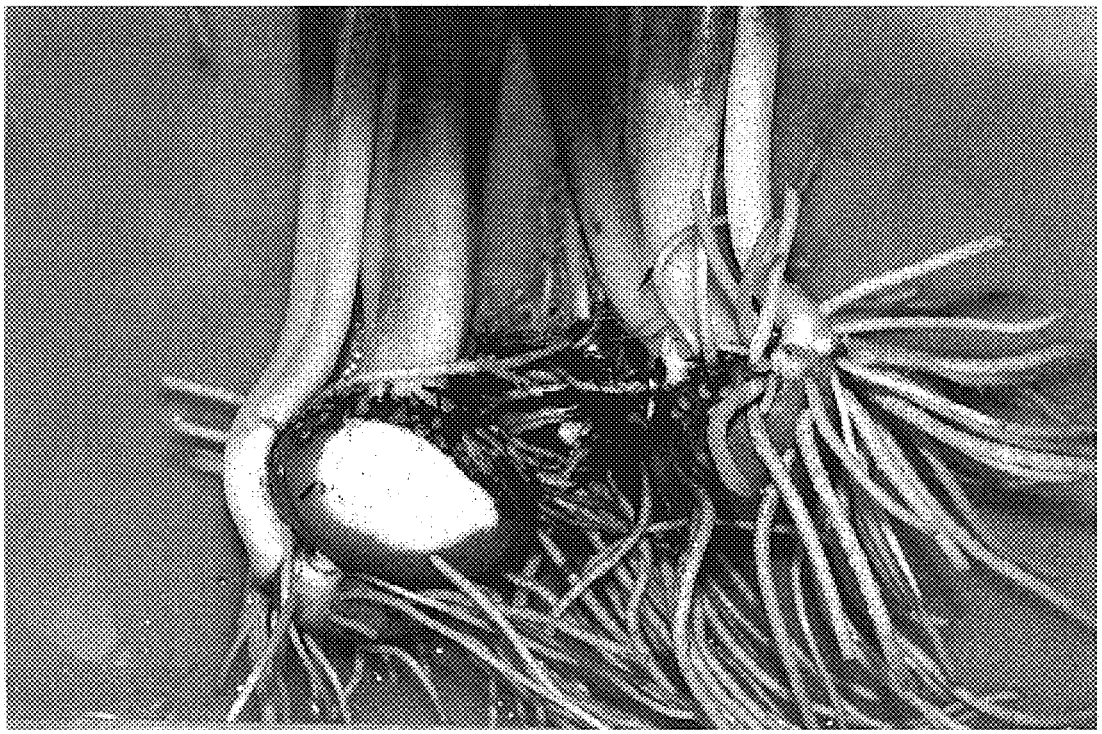

* * * * *